United States Patent
Sun

(10) Patent No.: US 6,402,825 B1
(45) Date of Patent: Jun. 11, 2002

(54) SURFACE MODIFIED CARBON BLACK

(75) Inventor: Jing X Sun, Lexington, KY (US)

(73) Assignee: Lexmark International, Inc, Lexington, KY (US)

( * ) Notice: Subject to any disclaimer, the term of this patent is extended or adjusted under 35 U.S.C. 154(b) by 0 days.

(21) Appl. No.: 09/916,571

(22) Filed: Jul. 27, 2001

(51) Int. Cl.$^7$ ................................................. C09C 1/56
(52) U.S. Cl. ........................ 106/473; 106/472; 106/476; 106/477; 423/449.2
(58) Field of Search ................................. 106/472, 473, 106/476, 477; 423/449.2

(56) References Cited

U.S. PATENT DOCUMENTS

| | | |
|---|---|---|
| 2,641,533 A | 6/1953 | Cines et al. |
| 4,994,520 A | 2/1991 | Mori et al. |
| 5,736,606 A | 4/1998 | Yanagi et al. |
| 5,846,307 A | 12/1998 | Nagasawa et al. |
| 5,861,447 A | 1/1999 | Nagasawa et al. |
| 5,907,009 A * | 5/1999 | Muraoka et al. ............ 252/511 |
| 5,968,244 A | 10/1999 | Ueda et al. |
| 5,976,233 A | 11/1999 | Osumi et al. |
| 6,132,502 A | 10/2000 | Yatake |
| 6,153,001 A | 11/2000 | Suzuki et al. |
| 6,255,412 B1 * | 7/2001 | Wang et al. ................. 524/496 |

FOREIGN PATENT DOCUMENTS

| | | |
|---|---|---|
| EP | 289624 | 12/1992 |
| JP | 62-112662 * | 5/1987 |
| WO | WO 97/49774 | 6/1997 |

* cited by examiner

*Primary Examiner*—Anthony Green
(74) *Attorney, Agent, or Firm*—David E. LaRose; Jacqueline M. Daspit

(57) ABSTRACT

The invention provides a surface modified carbon black and method for production. The surface modified carbon black is produced by reacting self-dispersing or oxidized carbon with a steric inducing compound via an organic acid halide intermediary. The steric inducing compounds are substantially soluble in the organic components of an ink composition and are reactive with an organic acid halide. Electrostatic and steric stability are provided by the surface modified carbon black. The surface modified carbon black exhibits solubility in aqueous and organic media and exhibits excellent resistance to coagulation within an ink jet printhead.

19 Claims, No Drawings

SURFACE MODIFIED CARBON BLACK

FIELD OF THE INVENTION

The invention relates to improved carbon black and methods for making improved carbon black for use in ink formulations, particularly ink jet printers.

BACKGROUND OF THE INVENTION

Ink jet recording is an advantageous print method used in many commercial products. Beneficial characteristics include small size, high speed, low cost, and adaptability to various substrates. A common problem with ink jet recording systems involves the formulation of an ink composition that has ideal print characteristics. Dyes are often used in ink compositions, but dyes are prone to fading and poor water fastness which adversely effect print quality. Accordingly, pigments are used in ink compositions to improve the light fastness and water fastness of ink. Of the pigments used in ink formulation, carbon black is one of the most commonly used pigments. Unfortunately, carbon black is not readily soluble in aqueous solutions.

Direct oxidation of carbon black generates carboxy (COOH) groups on the surface of the carbon black which provides a self-dispersing carbon black in aqueous compositions. Such carbon black exhibits increased electrostatic stability. However, the electrostatic stability is sensitive to other characteristics of the ink composition. In particular, electrostatic stability is very sensitive to the pH and electrolyte concentration. Accordingly, self-dispersing carbon black is prone to coagulation especially within the nozzle of an ink jet print system. Furthermore, such self-dispersing carbon black is not readily soluble with the other components of the ink composition such as humactants and binders.

Improving the solubility of carbon black while reducing the need for a dispersant has been the focus of much research. For example, U.S. Pat. No. 5,630,868 to Belmont et al. and U.S. Pat. No. 5,672,198 to Belmont disclose the use of a diazonium salt to attach water soluble functional groups to the surface of carbon black. However, the functional groups may be attached only by use of a very specific diazotization reaction. There is a limitation with respect to the type of functional groups which may be attached to carbon black by such a reaction mechanism because hydrophilic polymers terminated with aromatic amines required for conducing the reaction are typically not commercially available. Accordingly, a separate reaction is required to form such hydrophilic compounds thereby increasing the cost of producing modified carbon black according to this technique.

A need exists for a surface modified carbon black that may be readily soluble in water while providing improved stability within ink formulations containing organic components.

SUMMARY OF THE INVENTION

The present invention relates to a method of producing a surface modified carbon black having enhanced stability in an ink composition. According to the invention a self-dispersing or oxidized carbon black is reacted with a thionyl halide to produce acid halide groups on the surface of the carbon black. The acid halide modified carbon black is subsequently reacted with a steric inducing compound which is readily soluble in the organic components of the ink composition and is reactive with the acid halide groups.

An advantage of the invention is that the surface modified carbon black exhibits both electrostatic and steric stability. The electrostatic and steric stability is maintained within varying pH levels and electrolyte concentrations. A further advantage of the surface modified carbon black is that it is self-dispersible in water and in the organic components of the ink composition. Another advantage is that the surface modified carbon black resists coagulation as the aqueous components of the ink evaporate during heat application within the ink jet printhead.

An important advantage of the invention is the significant increase in idle time exhibited by representative ink formulations made with the surface modified carbon black. Without desiring to be bound by theoretical considerations, it is believed that as water evaporates from the ink adjacent the nozzles of a printhead, the properties of the ink composition in the printhead change. Ink formulations used in ink jet printers are a mixture of water, self-dispersing pigment and organic components such as humectants, binders, penetrants, organic solvent and the like. As water evaporates from the ink, the percentage of organic components in the ink formulation increases so that the ink becomes less hydrophilic. As the ink becomes less hydrophilic, the self-dispersing pigment which is strongly hydrophilic is pulled back into the bulk aqueous phase. Idle time is used to measure the short term reliability of the ink. "Idle time" means the time between nozzle firings just before the printhead produces delayed or misdirected ink droplets. Historically, self-dispersing carbon blacks exhibit poor idle times in ink jet printers. The invention to greatly improves the idle time of the ink formulation by modifying the surface of the pigment particles so that the particles remain substantially dispersed in the organic components as well as the aqueous components of the ink formulation.

DETAILED DESCRIPTION OF THE PREFERRED EMBODIMENTS

The surface modified carbon black of the present invention involves adding steric inducing groups to the surface of a carbon black. The carbon black to which the steric groups are added is preferably an oxidized carbon black. Methods for making an oxidized carbon black are well known and include reacting carbon black with sodium hypochlorite in an aqueous medium. The proportion by weight of sodium hypochlorite to provide an oxidized carbon black is preferably in a range from about 0.4 to about 5.25 parts hypochlorite per part carbon black by weight. U.S. Pat. No. 3,347,632 to Parker describes a preferred method for making oxidized carbon black and the disclosure is incorporated by reference as if fully set forth herein. A particularly preferred carbon black for making oxidized carbon black is neutral carbon black available from Cabot Corporation of Billerica, Mass. under the trade name MONARCH 880.

As a result of the reaction between carbon black and sodium hypochlorite, the surface of the carbon black contains carboxyl, hydroxyl, and/or carbonyl groups. The carboxyl groups on the surface of the carbon black provide sites for reaction with steric inducing compounds. Oxidized carbon black for reaction according to the invention preferably has an acid number ranging from about 0.5 to about 1.5 milliequivalents COOH/gram of carbon black.

As a first step in the reaction, oxidized carbon black is reacted with an amount of thionyl halide to provide organic acid halide groups on the surface of the carbon black. The halide groups of the thionyl halide may be a chloride, bromide, iodide, or fluoride group. Of the thionyl halides, thionyl chloride is a preferred thionyl halide which provides organic acid chloride groups on the surface of the carbon black. The amount of thionyl halide reacted with the carbon black preferably ranges from about 1 to about 20 mole equivalents per COOH group on the carbon black with approximately 10 mole equivalents per COOH group on the carbon black being most preferred. It is preferred to react all of the acid groups on the carbon black with thionyl halide, hence the use of excess thionyl halide is preferred which may also act as a solvent for the reaction.

The reaction between the carboxyl modified carbon black and the thionyl halide is preferably carried out in the presence of a solvent. The preferred solvent is an inert organic solvent. The particularly preferred solvents include, but are not limited to, methylene chloride, tetrahydrofuran, xylene, chloroform, 1,4-dioxane, toluene and other aprotic solvents.

While the order of reactant addition is not limited, the preferred order includes the addition of the thionyl halide to the solvent. Subsequently, this solution is added to a reaction vessel containing the oxidized carbon black.

The reaction is preferably conducted under an atmosphere of inert gas. A particularly preferred inert gas atmosphere for conducting the reaction is a nitrogen gas atmosphere. During the reaction, the temperature of the reaction mass is preferably controlled at a range from about 30° C. to about 55° C. Depending upon the solvent used, reflux may occur. Reaction times may range from about 4 to about 8 hours during which the reaction mass is stirred.

After reacting the oxidized carbon black with thionyl halide, the resulting carbon black having acid halide groups on the surface is isolated from the reaction mixture. Preferably, the reaction product is cooled to about 0° C. to about 5° C. After cooling, the product is filtered under a vacuum and is then washed with a dry solvent. In an alternate purification method, the reaction product is vacuum distilled to yield carbon black having acid halide groups on the surface thereof to provide an acid halide modified carbon black.

The acid halide modified carbon black is then reacted with a predetermined amount of a steric inducing compound. The amount of the steric inducing compound reacted with the carbon black preferably ranges from about 0.2 to about 0.9 milliequivalents per milliequivalent of acid halide modified carbon black. A preferred class of steric inducing compounds include monoalkoxy-terminated polyalkylene glycol compounds comprising an alkylene group containing from 2 to 6 carbon atoms and an alkyl group containing from 1 to 6 carbon atoms. Representative monoalkoxy-terminated polyalkylene glycol compounds include, but are not limited to triethylene glycol monomethyl ether, diethylene glycol monomethyl ether, triethyleneglycol monoethyl ether, diethylene glycol monoethyl ether, triethylene glycol monopropyl ether, diethyl ene glycol monopropyl ether, triethyl ene glycol monobutyl ether, diethylene glycol monobutyl ether and the like and mixtures thereof.

Other mono-terminated glycol reactants may be reacted with the acid halide modified carbon black to lower the acid number of the carbon black without adversely affecting the water dispersibility thereof. Such glycol reactants have weight average molecular weights ranging from about 100 to about 1000 and include, but are not limited to, methoxypolyethylene glycol, poly(ethylene glycol) tetrahydrofurfuryl ether, polyoxyethylene or polypropylene oxide nonyl phenyl ether and substituted derivatives of phenyl ether and nonyl phenyl ether.

Mono-amine terminated compounds may also be used as the steric inducing compound provided they are soluble in the organic components of the ink composition and reactive with an organic acid halide. Such compounds include, but are not limited to, alkoxy-terminated Jeffamine polyalkylene glycols having a weight average molecular weight ranging from about 500 to about 2500, methoxy-terminated Jeffamine polyethylene glycol, methoxy-tenninated Jeffamine polypropylene glycol and methoxy-terminated Jeffamine polyethylene glycol/polypropylene glycol copolymer. The Jeffamine compounds contain primary amino groups attached to the terminus of a polyether backbone also referred to as "polyether amines." The polyether backbone is based either on propylene oxide (PO), ethylene oxide (EO), or mixed EO/PO. Such amine-terninated compounds may be primary amines or secondary amines.

Other compounds reactive with the organic acid halide groups on the carbon black and soluble in the organic components of the ink composition include, but are not limited to, mono-hydroxy containing compounds such as 2-hydroxyethylpyrrolidone, 2-hydroxyethylmorpholine and 2-hydroxyethyl-oxazolidone and the like.

The reaction between the acid halide groups on the carbon black and the steric inducing compound is preferably carried out in the presence of an amount of inert solvent. The preferred solvent is an organic solvent. Particularly preferred solvents include, but are not limited to, methylene chloride, tetrahydrofuran, xylene, chloroform, 1,4-dioxane, toluene and other aprotic solvents.

The reaction mass also preferably includes a weak base which inhibits reaction by-products of hydrohalic acids. The preferred base is an amine and, most preferably, a tertiary amine. A particularly preferred tertiary amine is triethylamine. The preferred amount of tertiary amine in the reaction mass preferably ranges equivalent to the milliequivalents of organic acid halide in the reaction mass. Another useful amine for inhibiting by-product reactions includes pyridine.

While the order of reactant addition is not limited, the preferred order consists of the addition of the organic solvent to the reaction vessel containing the acid halide modified carbon black. Subsequently, the tertiary amine and the steric inducing compound are added dropwise to the reaction mass in solution with an organic solvent.

During the addition of reactants, the reaction mixture is preferably maintained at a temperature ranging from about 0° C. to about 5° C. The mixture is also preferably stirred for about to about 24 hours during which time the reaction is allowed to warm to room temperature, which is preferably between about 18° C. to about 24° C. When the reaction is substantially complete, the resulting mixture is treated to remove the solvent. The preferred treatment is vacuum distillation. An alternate treatment includes drying the mixture in an oven. An oven temperature of about 60° C. to about 80° C. is preferred with a dry time of about 30 to about 90 minutes.

Once purified, the mixture is washed with water and redispersed in a basic aqueous solution. The basic solution preferably consists of a metal or ammonium hydroxide with the metal being selected from the group consisting of alkali metals, alkaline earth metals, and transition metals. A particularly preferred basic solution is a 20% solution of potassium hydroxide. A sufficient amount of basic solution is added to the product to achieve a predetermined pH in the range from about 7.0 to about 8.5. The basic solution and carbon black product are preferably mixed for about 10 to about 60 minutes to remove any remaining free acid and/or halide ions from the product and to obtain the predetermined pH.

The surface modified carbon black made according to the foregoing procedure has an acid number preferably ranging from about 0.1 to about 0.7 milliequivalents COOH/gram of carbon black. It is further preferred that the surface modified carbon black have an average particle size ranging from about 100 to about 200 nanometers.

The following examples are given for illustrative purposes and are not meant in any way to limit the invention.

EXAMPLE 1

Carbon black was modified by mixing 40 grams of self-dispersing carbon black having 0.95 milliequivalents of COOH per gram of carbon black on the surface thereof with 30 grams of thionyl chloride and 100 mL of dry methylene chloride in a three neck flask equipped with a condenser, stirrer and nitrogen purge line. The mixture was stirred and heated to reflux for 7 hours, then cooled to a temperature ranging from about 0° to about 5° C. The resulting carbon black product was filtered under vacuum, washed with dry methylene chloride and stored in a sealed flask.

Methoxy polyethylene glycol (12 grams) having a weight average molecular weight of about 350 was added to a second three neck flask. Dry methylene chloride (100 mL) and 3.6 grams of triethylamine was added to the glycol in the flask and the mixture was cooled to 5° C. in an ice bath. The carbon black roduct from the first reaction was added slowly to the mixture in the second flask nder a nitrogen while stirring the mixture and maintaining the temperature at 5° C. When all of the carbon black product had been added, the mixture was stirred overnight at 5° C. The mixture was then oven dried at a temperature ranging from about 60° to about 80° C. for an hour and the dried product was washed with 500 mL of deionized water. The final product was redissolved in potassium hydroxide to obtain a pH of 7.5. Once the pH of 7.5 was obtained, the mixture was stirred in a high speed mixer such as a high speed mixer from Tekmar Dohrmann of Mason, Ohio under the trade name TISSUMIZER for an hour. The particle size of the product was 148 nm. Ultrafiltration was used to farther purify the product. The product was titrated and contained 0.115 milliequivalents of COOH/gram of carbon black.

EXAMPLE 2

Carbon black was modified by mixing 40 grams of self-dispersing carbon black having about 0.95 milliequivalents of COOH per gram of carbon black on the surface thereof with mole equivalents of thionyl chloride and 150 mL of toluene in a three neck flask equipped with a condenser, stirrer and nitrogen purge line. The mixture was stirred and heated to 50° C. and reacted for hours under a nitrogen atmosphere. The resulting carbon black product was vacuum distilled under 100 mm Hg vacuum at 50° C. to remove the solvent and unreacted thionyl chloride. The carbon product having surface acid chloride groups was cooled to a temperature ranging from about 0° to about 5° C. in an ice bath.

Cold methylene chloride (100 mL) was added to the flask, then 24 milliequivalents (24 grams) of Jeffamine STJ506 (MW 1000) from Huntsman Corporation of Salt Lake City, Utah and 3.3 grams of triethylamine in 20 mL of methylene chloride was added dropwise to the flask. The reaction mixture was stirred overnight at room temperature. The flask containing the reaction product was distilled under vacuum to remove the solvent, then washed with water to remove the triethylaminehydrochloric acid salt. The final product was redispersed in 20% KOH to obtain a pH of 8.0.

Example 3

In the following Table 1, ink formulations were prepared with self-dispersing carbon black and with self-dispersing carbon black chemically modified to contain steric inducing groups derived from triethylene glycol monomethyl ether. Samples 1, 2 and 5 in the table contained self-dispersing carbon black in the amount indicated and carbon black dispersed in a terpolymer made according to U.S. Pat. No. 5,714,538 to Beach et al. All of the other components of the formulations are substantially the same, with the exception that samples 2 and 4 have an increased amount of ACRYJET 3666 binder and a reduced amount of deionized water.

Each of samples 5, 6 and 7 were use in three ink cartridges and images were printed with the cartridges to determine idle time. Longer idle times are desirable from a printer operation point of view. Idle time for an ink formulation was determined by first printing reference droplets for all nozzles from an ink cartridge at time zero on a print media. The cartridge was then allowed to idle for specific intermittent periods of time before again firing the same nozzles to print test drops in vicinity of the reference droplets. The idle time was increased incrementally between nozzle firings. The position of the test drops on paper were compared with the reference droplets. The period of time between nozzle firings at which the test drops are delayed or misdirected with respect to the reference droplets is noted and specified as the idle time.

TABLE 1

| Component | Sample 1 | Sample 2 | Sample 3 | Sample 4 | Sample 5 | Sample 6 | Sample 7 |
| --- | --- | --- | --- | --- | --- | --- | --- |
| SDCB[1] | 2.5 | 2.5 | — | — | 2.5 | — | — |
| ESDCB[2] | — | — | 2.5 | 2.5 | — | 2.5 | 2.5 |
| Dispersed Carbon Black[3] (20 wt. % solids in terpolymer) | 3 | 3 | 3 | 3 | — | — | — |
| Dispersed Carbon Black[3] (16.67 wt. % solids in terpolymer) | — | — | — | — | 3 | 3 | 3 |
| 2-pyrrolidone | 7.5 | 7.5 | 7.5 | 7.5 | 7.5 | 7.5 | 7.5 |
| 1,2-hexanediol | 1.2 | 1.2 | 1.2 | 1.2 | 1.2 | 1.2 | 1.2 |
| Hexyl carbitol | 0.4 | 0.4 | 0.4 | 0.4 | 0.4 | 0.4 | 0.4 |
| ACRYJET 3666 (23.8 wt. % resin solids) | 2.1 | 6.3 | 2.1 | 6.3 | 2.1 | 2.1 | 2.1 |
| Polyethylene glycol (MW 400) | 7.5 | 7.5 | 7.5 | 7.5 | 7.5 | 7.5 | 7.5 |

TABLE 1-continued

| Component | Sample 1 | Sample 2 | Sample 3 | Sample 4 | Sample 5 | Sample 6 | Sample 7 |
|---|---|---|---|---|---|---|---|
| Dionized water | 75.8 | 71.6 | 75.8 | 71.6 | 75.8 | 75.8 | 75.8 |
| Total | 100 | 100 | 100 | 100 | 100 | 100 | 100 |
| P. Size | 110 | 123 | 161 | 173 | 126 | 200 | 180 |
| Optical density | 1.28 | 1.26 | 1.11 | 1.14 | 1.29 | 1.29 | 1.28 |
| Idle time (sec.) | 6 | 2 | 36 | 36 | 10 | >30 | >30 |
| Drying time (sec.) | 9.7 | 8.8 | 8.8 | 8.4 | — | — | — |

[1] Self-dispersing carbon black
[2] Esterified, self-dispersing carbon black made according to Example 1.
[3] Carbon black dispersed in an acrylic terpolymer made by polymerizing methacrylic acid, stearyl methacrylate, and dimethylsiloxane, according to U.S. Pat. No. 5,714,538 to Beach et al.

As shown by the comparisons in Table 1, ink formulations 3, 4, 6 and 7 containing modified self-dispersing carbon black according to the invention exibited substantially longer idle times than ink formulations containing un-modified self-dispersing carbon black. Idle times using the ink formulations of the invention were generally in the 30 second and greater range, whereas idle times of 2 to 12 seconds were exhibited by samples 1, 2 and 5.

It is contemplated, and will be apparent to those skilled in the art from the foregoing specification that modifications and/or changes may be made in the embodiments of the invention. Accordingly it is expressly intended that the foregoing are only illustrative of the preferred embodiments and are not limiting thereto and that the true spirit and scope of the present invention be determined by reference to the appended claims.

What is claimed is:

1. A method for producing surface modified carbon black comprising the steps of:
   reacting the carbon black containing surface carboxyl groups with thionyl halide under conditions sufficient to produce acid halide groups on the surface of the carbon black; and
   reacting carbon black containing acid halide groups on the surface thereof with a steric inducing compound selected from compounds which are readily soluble in organic components of an ink composition and which are reactive with the acid halide groups to provide a surface modified carbon black.

2. The method for producing surface modified carbon black according to claim 1, wherein the carbon black reacted with the thionyl halide has an acid number of about 0.5 to about 1.5 milliequivalents COOH/gram of carbon black.

3. The method for producing surface modified carbon black according to claim 1, wherein the thionyl halide comprises thionyl chloride.

4. The method for producing surface modified carbon black according to claim 1, wherein the carbon black is reacted with thionyl halide in the presence of a solvent.

5. The method for producing surface modified carbon black according to claim 4, wherein the solvent comprises methylene chloride.

6. The method for producing surface modified carbon black according to claim 4, wherein the solvent comprises toluene.

7. The method for producing surface modified carbon black according to claim 1, wherein the steric inducing compound is a monoalkoxy-terminated polyalkylene glycol compound.

8. The method for producing surface modified carbon black according to claim 7, wherein the steric inducing compound comprises an alkylene group containing from 2 to 6 carbon atoms and an alkoxy group containing from 1 to 6 carbon atoms.

9. The method for producing surface modified carbon black according to claim 7, wherein the steric inducing compound comprises a glycol compound with a weight average molecular weight ranging from about 100 to about 1000.

10. The method for producing surface modified carbon black according to claim 7, wherein the steric inducing compound comprises a glycol compound selected from the group consisting of methoxypolyethylene glycol and poly(ethylene glycol) tetrahydrofurfuryl ether.

11. The method for producing surface modified carbon black according to claim 1, wherein the steric inducing compound is a mono-amine terminated compound.

12. The method for producing surface modified carbon black according to claim 11, wherein the mono-amine terminated compound comprises a Jeffamine derivative.

13. The method for producing surface modified carbon black according to claim 1, wherein the steric inducing compound comprises a mono-hydroxy containing compound selected from the group consisting of 2-hydroxyethylpyrrolidinone, 2-hydroethylmorpholine, and 2-hydroxyethyloxazolidone.

14. The method for producing surface modified carbon black according to claim 1, wherein the surface modified carbon black has an acid number ranging from about 0.1 to about 0.7 milliequivalents COOH/gram of carbon black.

15. The method for producing surface modified carbon black according to claim 1, wherein the surface modified carbon black has an average particle size ranging from about 80 to about 200 nanometers.

16. A surface modified carbon black made by the method of claim 1.

17. A surface modified carbon black for use in ink jet printer ink formulations, the carbon black having a surface containing a steric inducing group attached thereto and having an acid number ranging from about 0.1 to about 0.7 milliequivalents COOH/gram of carbon black.

18. The surface modified carbon black according to claim 17, wherein the average particle size ranges from about 80 to about 200 nanometers.

19. The surface modified carbon black according to claim 17, wherein the steric inducing group is derived from a steric inducing compound selected from the group consisting of a monoalkoxy-terminated polyalkylene glycol, a mono-amine terminated polyalkylene glycol compound, 2-hydroxyethylpyrrolidinone, 2-hydroethylmorpholine, and 2-hydroxyethyloxazolidone.

* * * * *

UNITED STATES PATENT AND TRADEMARK OFFICE
CERTIFICATE OF CORRECTION

PATENT NO. : 6,402,825 B1
DATED : June 11, 2002
INVENTOR(S) : Jing X Sun

It is certified that error appears in the above-identified patent and that said Letters Patent is hereby corrected as shown below:

Column 2,
Line 30, delete the word "to" after "invention" and before "greatly"
Line 46, change "hypochiorite" to -- hypochlorite --

Column 4,
Line 8, change "methoxy-tenninated" to -- methoxy-terminated --
Line 49, change "about to about 24 hours" to -- about 10 to about 24 hours --

Column 5,
Line 30, change "black roduct from" to -- black product from --
Line 31, change "nder" to -- under --
Line 43, change "farther" to -- further --

Column 6,
Line 2, change "with mole equivalents" to -- with 10 mole equivalents --
Line 5, change "for hours" to -- for 5 hours --
Line 31, change "terpolymcr" to -- terpolymer --

Column 7,
Line 18, change "exibited" to -- exhibited --

Signed and Sealed this

Second Day of March, 2004

JON W. DUDAS
*Acting Director of the United States Patent and Trademark Office*